(12) United States Patent
Huang et al.

(10) Patent No.: US 11,357,462 B2
(45) Date of Patent: Jun. 14, 2022

(54) 3D PERSPECTIVE INDICATOR AND GENERATION METHOD THEREFOR AND APPLICATION THEREOF

(71) Applicant: GE Precision Healthcare LLC

(72) Inventors: Yu Huang, Beijing (CN); Tiegong Zheng, Beijing (CN); Yanran Xu, Beijing (CN)

(73) Assignee: GE Precision Healthcare LLC, Wauwatosa, WI (US)

( * ) Notice: Subject to any disclaimer, the term of this patent is extended or adjusted under 35 U.S.C. 154(b) by 130 days.

(21) Appl. No.: 16/877,657

(22) Filed: May 19, 2020

(65) Prior Publication Data

US 2020/0375561 A1 Dec. 3, 2020

(30) Foreign Application Priority Data

May 31, 2019 (CN) .......................... 201910469864.0

(51) Int. Cl.
*A61B 6/00* (2006.01)
*A61B 6/03* (2006.01)
(Continued)

(52) U.S. Cl.
CPC .............. *A61B 6/466* (2013.01); *A61B 6/032* (2013.01); *A61B 6/0407* (2013.01);
(Continued)

(58) Field of Classification Search
CPC ....................... G06T 2207/10028; A61B 6/032
See application file for complete search history.

(56) References Cited

U.S. PATENT DOCUMENTS

2017/0224298 A1\* 8/2017 Hannemann ......... A61B 6/0492

FOREIGN PATENT DOCUMENTS

JP 2009285147 A 12/2009

OTHER PUBLICATIONS

JP 2009-285147 Machine Translation; 15 pages.
JP application 2020-093693 filed May 28, 2020—Office Action dated Oct. 12, 2021, Machine Translation; 6 pages.

\* cited by examiner

*Primary Examiner* — Dani Fox

(57) ABSTRACT

The present invention relates to a 3D perspective indicator and a generation method therefor and an application thereof. The present invention specifically provides a 3D perspective indicator for a CT system and a generation method therefor as well as a method and an apparatus for controlling a scanning range in a CT system. The method for generating a 3D perspective indicator comprises: generating an upper boundary plane and a lower boundary plane perpendicular to a scanning direction and an auxiliary plane perpendicular to the upper boundary plane and the lower boundary plane in a coordinate system space of the CT system, the auxiliary plane being located above a to-be-scanned part of a patient; and identifying an upper contour line intersecting the upper boundary plane and a lower contour line intersecting the lower boundary plane in a point cloud generated based on a depth image of the patient, wherein the 3D perspective indicator comprises the upper contour line and the lower contour line, the upper boundary plane and the lower boundary plane, and the auxiliary plane. The present invention further provides a CT system using the apparatus and a computer-readable storage medium capable of implementing the method.

19 Claims, 7 Drawing Sheets

(51) Int. Cl.
*A61B 6/04* (2006.01)
*G06T 7/50* (2017.01)
*G06T 7/00* (2017.01)
(52) U.S. Cl.
CPC ............ *A61B 6/5223* (2013.01); *A61B 6/547* (2013.01); *G06T 7/0012* (2013.01); *G06T 7/50* (2017.01); *G06T 2207/10028* (2013.01); *G06T 2207/30004* (2013.01)

3D PERSPECTIVE INDICATOR AND GENERATION METHOD THEREFOR AND APPLICATION THEREOF

CROSS-REFERENCE TO RELATED APPLICATIONS

This application claims priority to Chinese Patent Application No. 201910469864.0 filed on May 31, 2019, the disclosure of which is herein incorporated by reference in its entirety.

TECHNICAL FIELD

The present invention relates to a computed tomography (CT) system, and particularly, to a three-dimensional (3D) perspective indicator for a CT system and a generation method therefor as well as a method and an apparatus for controlling a scanning range in a CT system. The present invention further particularly relates to a CT system using the apparatus and a computer-readable storage medium capable of implementing the method.

BACKGROUND

In conventional CT scanning, an operator needs to first instruct a patient to lie down on a CT scanning bed, and then manually move the CT scanning bed and use a laser lamp in a CT scanning gantry to determine baselines and landmarks for scanning. The scanning range is determined by an offset, while the offset is determined by parameter values that need to be set on a console outside a scanning room. This approach does not provide an intuitive way for the operator to understand the scanning range and requires the operator to operate both inside and outside the scanning room.

Some prior art also exists that attempt to display a scanning range with a two-dimensional (2D) image, but it is still difficult for an operator to determine the scanning volume of a patient on the 2D image due to perspective distortion.

Therefore, an urgent need exists for a technology to address the aforementioned problems in CT scanning.

SUMMARY

The objective of the present invention is to overcome the aforementioned problems and/or other problems in the prior art. The present invention helps an operator to determine and control a 3D volume to be scanned through a newly built 3D perspective indicator, thereby providing an intuitive, precise and efficient way for the operator to complete all pre-scanning operations in a scanning room.

According to a first aspect of the present invention, a method for generating a 3D perspective indicator in a CT system is provided, the method comprising: generating an upper boundary plane and a lower boundary plane perpendicular to a scanning direction and an auxiliary plane perpendicular to the upper boundary plane and the lower boundary plane in a coordinate system space of the CT system, the auxiliary plane being located above a to-be-scanned part of a patient; and identifying an upper contour line intersecting the upper boundary plane and a lower contour line intersecting the lower boundary plane in a point cloud generated based on a depth image of the patient, wherein the 3D perspective indicator comprises the upper contour line and the lower contour line, the upper boundary plane and the lower boundary plane, and the auxiliary plane.

According to a second aspect of the present invention, a 3D perspective indicator for a CT system is provided, comprising: an upper boundary plane and a lower boundary plane, which are in a coordinate system space of the CT system and perpendicular to a scanning direction; an auxiliary plane being in the coordinate system space of the CT system and perpendicular to the upper boundary plane and the lower boundary plane, the auxiliary plane being located above a to-be-scanned part of a patient; and an upper contour line and a lower contour line, which are located in a point cloud generated based on a depth image of the patient and respectively intersect the upper boundary plane and the lower boundary plane.

The upper contour line and the lower contour line, the upper boundary plane and the lower boundary plane, and the auxiliary plane that are generated in the aforementioned method represent a 3D perspective space superimposed on a 2D image or video. The space resembles a virtual perspective "box," where the scanning range of CT scanning on the patient is within this perspective "box." This newly built 3D perspective space is equivalent to an indicator through which an operator can view and modify the scanning range. A 3D impression is generated for the volume of the patient to be scanned so that the operator can control the scanning range intuitively, accurately and conveniently without any perspective distortion.

Preferably, a patient structure model extracted from the point cloud may be introduced into the method for generating a 3D perspective indicator and the 3D perspective indicator described above, the upper contour line and the lower contour line being respectively intersecting lines of the patient structure model with the upper boundary plane and the lower boundary plane.

More preferably, a main reference plane parallel to the auxiliary plane may be generated in the coordinate system space of the CT system, the patient structure model being on the main reference plane and, together with the main reference plane, defining a shape of the to-be-scanned part.

Thus, the aforementioned patient structure model is introduced to determine, together with the main reference plane, the shape of the to-be-scanned part of the patient, so that the body shape of the patient at a scanning start position and a scanning end position can be presented more intuitively and precisely.

The main reference plane may be generated on a highest surface of a scanning bed.

Further, the upper contour line and/or lower contour line may intersect the main reference plane at upper boundary reference points and/or lower boundary reference points, and the upper contour line and/or the lower contour line matches a contour of the to-be-scanned part of the patient.

Still further, the upper boundary reference points and/or the lower boundary reference points are two reference points across the patient structure model, and a distance therebetween is greater than a maximum width of the patient structure model.

Furthermore, the two upper boundary reference points and/or two lower boundary reference points are forward-projected onto the auxiliary plane, so that two upper boundary auxiliary points and/or two lower boundary auxiliary points can be obtained.

In the method for generating a 3D perspective indicator and the 3D perspective indicator according to the present invention, the upper boundary plane and the lower boundary plane are capable of separately moving or simultaneously moving in the scanning direction.

Preferably, when the upper boundary plane and/or the lower boundary plane moves in the scanning direction, the upper contour line and/or the lower contour line changes in real time with the to-be-scanned part of the patient.

More preferably, the real-time change is continuous.

According to a third aspect of the present invention, a method for controlling a scanning range in a CT system is provided, the method comprising: generating a 3D perspective indicator in the CT system by the method for generating a 3D perspective indicator in a CT system described above; and controlling a scanning range using the 3D perspective indicator, the upper contour line and the lower contour line, the upper boundary plane and the lower boundary plane, and the auxiliary plane representing the scanning range, wherein a region between the upper boundary plane and the lower boundary plane comprises the to-be-scanned part of the patient.

The method for controlling a scanning range in a CT system described above has the 3D perspective indicator described previously introduced therein, and thus is free from perspective distortion, and helps an operator to better understand a 3D volume to be scanned. Moreover, compared with the conventional method that needs to use a laser lamp to set scanning baselines and check a scanning range through parameters on a console outside a scanning room, the aforementioned method enables the operator to complete all pre-scanning work in the scanning room. Control operations on the scanning range are made more intuitive, accurate, and convenient, thereby greatly improving operation efficiency and eliminating manual errors in the conventional method.

Preferably, for the method for controlling a scanning range described above, the scanning range is displayed through a display unit, and the scanning range is controlled by translating the upper boundary plane and/or the lower boundary plane up and down in the scanning direction on the display unit.

Preferably, for the method for controlling a scanning range described above, the scanning range is displayed through a display unit, and the scanning range is controlled by setting on the display unit at least one of the two upper boundary auxiliary points and/or at least one of the two lower boundary auxiliary points and/or any point in a connection line of the two upper boundary auxiliary points and/or any point in a connection line of the two lower boundary auxiliary points.

Preferably, for the method for controlling a scanning range described above, the scanning range is displayed through a display unit, and the entire scanning range is controlled to translate up and down in the scanning direction by controlling on the display unit a connection line between the upper boundary auxiliary point and a corresponding lower boundary auxiliary point on the same side or any point in the connection line.

According to a fourth aspect of the present invention, a computer-readable storage medium is further provided, having encoded instructions recorded thereon, wherein when the instructions are executed, the method for generating a 3D perspective indicator and the method for controlling a scanning range described above are performed.

According to a fifth aspect of the present invention, an apparatus for controlling a scanning range in a CT system is provided, the apparatus comprising: a display unit, configured to display a scanning range represented by an upper contour line and a lower contour line, an upper boundary plane and a lower boundary plane, and an auxiliary plane; and a control unit, configured to generate an upper boundary plane and a lower boundary plane perpendicular to a scanning direction and an auxiliary plane perpendicular to the upper boundary plane and the lower boundary plane in a coordinate system space of the CT system, the auxiliary plane being located above a to-be-scanned part of a patient; and identify an upper contour line intersecting the upper boundary plane and a lower contour line intersecting the lower boundary plane in a point cloud generated based on a depth image of the patient, wherein a region between the upper boundary plane and the lower boundary plane comprises the to-be-scanned part of the patient.

Preferably, the apparatus may further comprise: a patient structure model unit, configured to extract a patient structure model from the point cloud, the upper contour line and the lower contour line being respectively intersecting lines of the patient structure model with the upper boundary plane and the lower boundary plane.

More preferably, the control unit may be further configured to generate a main reference plane parallel to the auxiliary plane in the coordinate system space of the CT system, the patient structure model being on the main reference plane and, together with the main reference plane, defining a shape of the to-be-scanned part.

The main reference plane may be generated on a highest surface of a scanning bed.

The upper contour line and/or lower contour line may intersect the main reference plane at upper boundary reference points and/or lower boundary reference points, and the upper contour line and/or the lower contour line matches a contour of the to-be-scanned part of the patient.

Further, the upper boundary reference points and/or the lower boundary reference points may be two reference points across the patient structure model, and a distance therebetween may be greater than a maximum width of the patient structure model.

Moreover, points obtained by forward-projecting the two upper boundary reference points and/or two lower boundary reference points onto the auxiliary plane are two upper boundary auxiliary points and/or two lower boundary auxiliary points.

Preferably, the control unit may be further configured to control the scanning range by translating the upper boundary plane and/or the lower boundary plane up and down in the scanning direction on the display unit.

More preferably, when the control unit controls the upper boundary plane and/or the lower boundary plane to move in the scanning direction, the upper contour line and/or the lower contour line changes in real time with the to-be-scanned part of the patient.

Moreover, the real-time change is continuous.

Preferably, the control unit may be further configured to control the scanning range by setting on the display unit at least one of the two upper boundary auxiliary points and/or at least one of the two lower boundary auxiliary points and/or any point in a connection line of the two upper boundary auxiliary points and/or any point in a connection line of the two lower boundary auxiliary points.

Preferably, the control unit may be further configured to control the entire scanning range to translate up and down in the scanning direction by controlling on the display unit a connection line between the upper boundary auxiliary point and a corresponding lower boundary auxiliary point on the same side or any point in the connection line.

The apparatus for controlling a scanning range in a CT system described above can completely implement the method for controlling a scanning range in a CT system described above. The apparatus and the method both can be applied to a CT system to enable an operator to intuitively and precisely control a CT scanning range in real time, and meanwhile can improve working efficiency and provide better nursing experience to a patient.

According to a sixth aspect of the present invention, a CT system is further provided, which may comprise the apparatus for controlling a scanning range described above.

Other features and aspects will become clear through the following detailed description, accompanying drawings, and claims.

BRIEF DESCRIPTION OF THE DRAWINGS

The present invention may be better understood by describing exemplary embodiments of the present invention with reference to accompanying drawings, in which.

DETAILED DESCRIPTION

Specific implementation manners of the present invention will be described in the following. It should be noted that during the specific description of the implementation manners, it is impossible to describe all features of the actual implementation manners in detail in this description for the sake of brief description. It should be understood that in the actual implementation of any of the implementation manners, as in the process of any engineering project or design project, a variety of specific decisions are often made in order to achieve the developer's specific objectives and meet system-related or business-related restrictions, which will vary from one implementation manner to another. Moreover, it can also be understood that although the efforts made in such development process may be complex and lengthy, for those of ordinary skill in the art related to content disclosed in the present invention, some changes in design, manufacturing, production or the like based on the technical content disclosed in the present disclosure are only conventional technical means, and should not be construed as that the content of the present disclosure is insufficient.

Unless otherwise defined, the technical or scientific terms used in the claims and the description are as they are usually understood by those of ordinary skill in the art to which the present invention pertains. The words "first," "second," and similar words used in the description and claims of the patent application of the present invention do not denote any order, quantity or importance, but are merely intended to distinguish between different constituents. "One," "a" and similar words are not meant to be limiting, but rather denote the presence of at least one. The word "include," "comprise" or a similar word is intended to mean that an element or article that appears before "include" or "comprise" encompasses an element or article and equivalent elements that are listed after "include" or "comprise," and does not exclude other elements or articles. The word "connect," "connected" or a similar word is not limited to a physical or mechanical connection, and is not limited to a direct or indirect connection.

According to an embodiment of the present invention, a method for generating a 3D perspective indicator in a CT system is provided.

Figure 1:
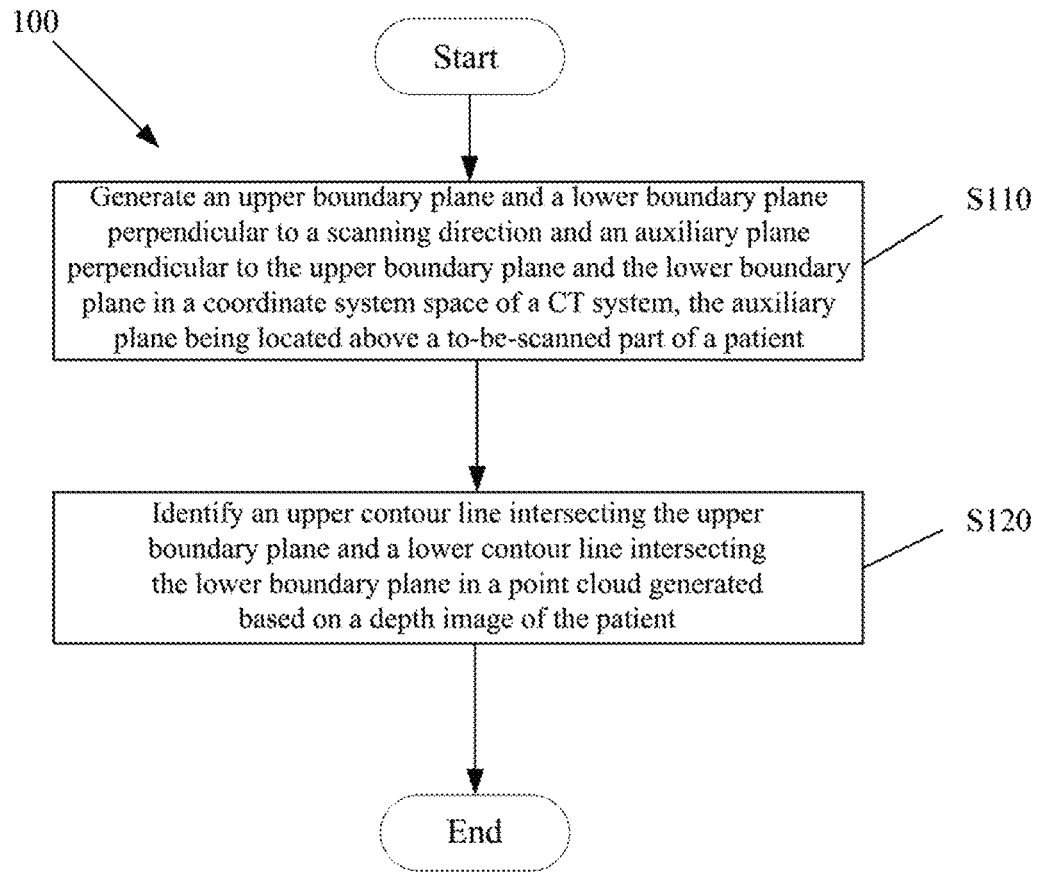
FIG. 1 is a flowchart of a method for generating a 3D perspective indicator in a CT system according to an exemplary embodiment of the present invention.
Figure 2:
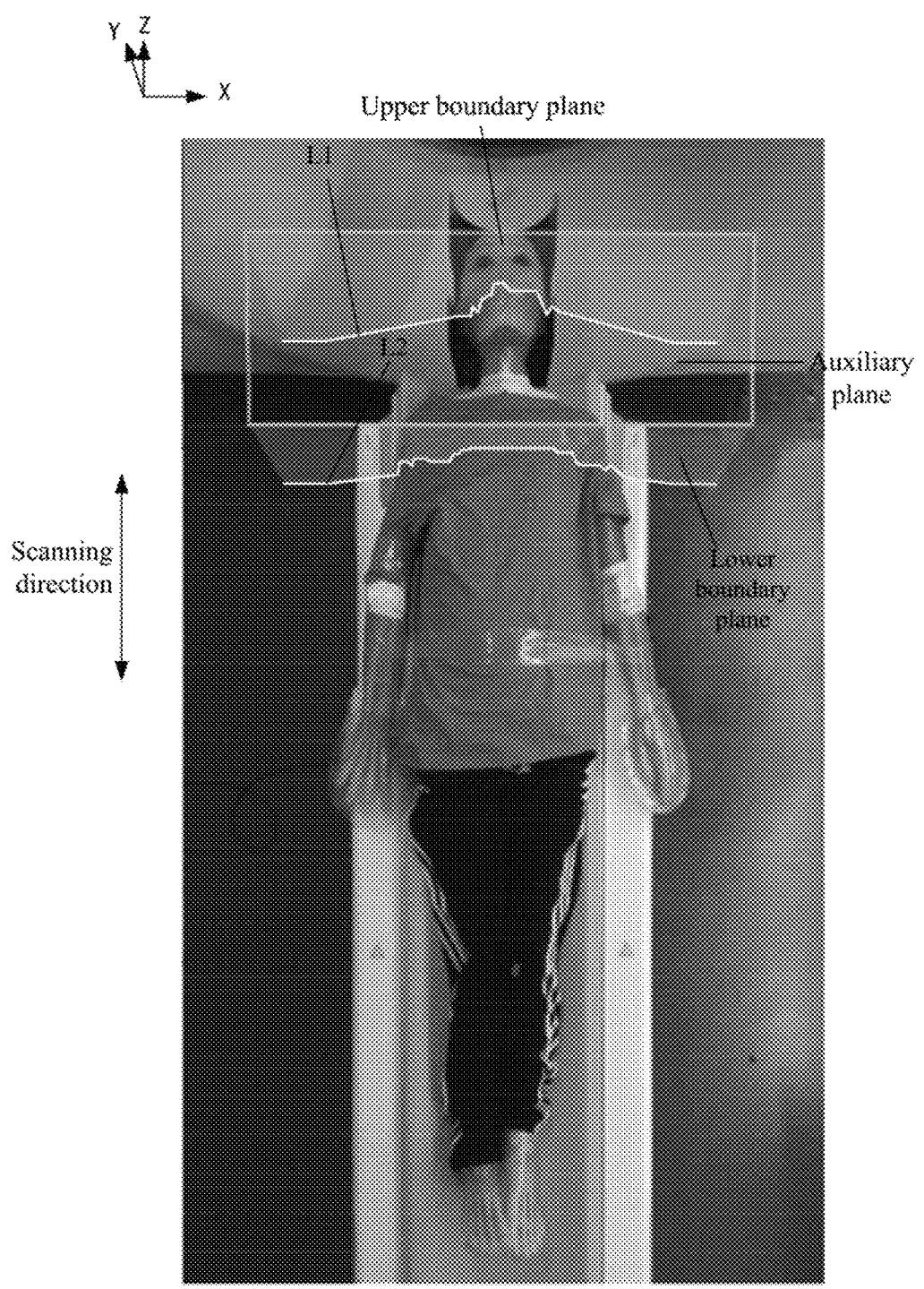
FIG. 2 is a schematic perspective view of a 3D perspective indicator according to an exemplary embodiment of the present invention.

FIG. 1 is a flowchart of a method 100 for generating a 3D perspective indicator in a CT system according to an exemplary embodiment of the present invention. The method 100 may include steps S110 to S120. Reference may be made to FIG. 2 as well, which is a schematic perspective view of a 3D perspective indicator according to an exemplary embodiment of the present invention.

As shown in FIG. 1, step S110: generate an upper boundary plane and a lower boundary plane perpendicular to a scanning direction and an auxiliary plane perpendicular to the upper boundary plane and the lower boundary plane in a coordinate system space of the CT system, the auxiliary plane being located above a to-be-scanned part of a patient.

As shown in FIG. 2, the upper boundary plane and the lower boundary plane are perpendicular to the scanning direction and respectively represent a start position and an end position of scanning to be received by the patient. The two boundary planes help the operator to determine the volume in a scanning range. As long as the auxiliary plane is at a position higher than the highest point of the to-be-scanned part of the patient, the auxiliary plane is perpendicular to the upper boundary plane and the lower boundary plane. The auxiliary plane is quite important for constructing a 3D perspective space. The auxiliary plane is located above the to-be-scanned part of the patient, thus helping to generate a 3D perspective for displaying the scanning range. The 3D perspective space constructed in this way not only reasonably determines the depth of the scanning range, but also intuitively and accurately defines the upper boundary and lower boundary of the volume to be scanned in the scanning direction.

Returning to FIG. 1, step S120: identify an upper contour line intersecting the upper boundary plane and a lower contour line intersecting the lower boundary plane in a point cloud generated based on a depth image of the patient.

FIG. 2 shows the upper contour line L1 and the lower contour line L2. L1 and L2 are located not only in the point cloud, but also in the upper boundary plane and the lower boundary plane respectively.

The aforementioned point cloud is a large data set of 3D coordinates generated based on continuously obtained depth images of the patient. Specifically, a depth image of the patient may be acquired in real time through a 3D camera installed above the patient's body and a scanning bed (for example, on a ceiling of a scanning room), but the depth image of the patient may also be acquired in real time by other means or tools.

Thus, the upper contour line L1 and the lower contour line L2, the upper boundary plane and the lower boundary plane, and the auxiliary plane that are obtained in the method 100 together represent a 3D perspective indicator.

The method for generating a 3D perspective indicator described above implements an indicator superimposed on a 2D image or video, where the operator can view and modify the scanning range in real time through the indicator. A 3D impression is generated for the volume of the patient to be scanned while completely eliminating the misguidance caused by perspective distortion, so that the operator can accurately, intuitively, and conveniently determine and adjust the scanning range.

Moreover, the real-time 2D image or video on which the 3D perspective indicator is superimposed may provide an additional user interface while intuitively controlling the scanning range, so as to provide other uses for the operator, for example, predicting a collision zone before self-moving of the scanning bed.

Further, a patient structure model extracted from the point cloud may be introduced into the method 100 for generating a 3D perspective indicator described above, the upper contour line L1 and the lower contour line L2 being respectively intersecting lines of the patient structure model with the upper boundary plane and the lower boundary plane. That is, the upper contour line L1 and the lower contour line L2 are respectively located in the patient structure model.

Figure 3:
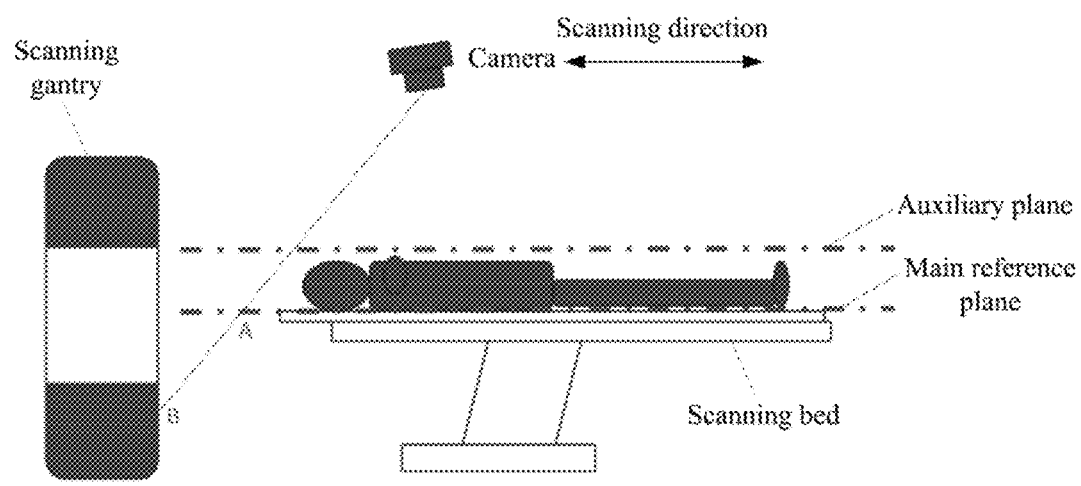
FIG. 3 is a schematic view illustrating an operation for generating a 3D perspective indicator in a CT system according to an exemplary embodiment of the present invention.

Furthermore, as shown in FIG. 3, in the method 100 for generating a 3D perspective indicator described above, a main reference plane parallel to the auxiliary plane may be generated in the coordinate system space of the CT system, the patient structure model being on the main reference plane and, together with the main reference plane, defining a shape of the to-be-scanned part. FIG. 3 shows a scanning bed and a scanning gantry in the CT system, and marks the position of the main reference plane.

The aforementioned patient structure model is in essence a large number of sets of points of three-dimensional coordinates; these sets take the form of a human being.

Thus, the aforementioned patient structure model is introduced to determine, together with the main reference plane, the shape of the to-be-scanned part of the patient, so that the body shape of the patient at a scanning start position and a scanning end position can be presented more intuitively and precisely, which provides an intuitive and precise volume representation for the operator, thereby controlling the scanning range more effectively and accurately. Moreover, when the operator uses the aforementioned generated 3D perspective indicator to modify the scanning range, the shape to be scanned can be updated according to the actual physical position (for example, the height of the scanning bed or the posture of the patient).

In addition, the presence of the main reference plane makes movement of the start position and the end position of the scanning range continuous and linear, and helps to select an appropriate position in a region containing neither the patient's body nor the scanning bed to provide a reasonable depth value for the scanning range.

Optionally, as shown in FIG. 3, the main reference plane is generated on a highest surface of the scanning bed. In the case that the scanning bed is designed to be concave in the middle in order to prevent the patient from falling off the scanning bed, the highest surface of the scanning bed is a surface formed at highest points on two sides of the scanning bed, but other cases where the highest surface of the scanning bed is the surface of other parts of the scanning bed are not excluded.

In FIG. 3, because of the presence of the main reference plane, a position A is selected in a region containing neither the patient's body nor the scanning bed, where the position A is in the main reference plane. That is, the depth of the scanning range does not exceed the position A in the highest surface of the scanning bed. Such selection is quite reasonable. However, if the main reference plane does not exist, a position B shown in FIG. 3 is probably selected to determine the depth of the scanning range. Although the position B is in a region containing neither the patient's body nor the scanning bed, the position B is on the scanning gantry. The scanning depth determined in this way is obviously quite unreasonable. The aforementioned main reference plane ensures that when the operator is about to adjust the start line (start position) or end line (end position) of the scanning range to a region outside the patient's body and the CT scanning bed, the moved start line or end line has its value in a Z axis of the CT coordinate system changing continuously and linearly, and will not eventually move out of the patient's body or the CT scanning bed.

It should be particularly noted that if the main reference plane is generated on the highest surface of the scanning bed as shown in FIG. 3, when the height of the scanning bed changes, the main reference plane needs to be regenerated according to the highest surface of the scanning bed after the change.

Further, the upper contour line L1 and/or lower contour line L2 may intersect the main reference plane at upper boundary reference points and/or lower boundary reference points. The upper contour line L1 and/or the lower contour line L2 matches a contour of the to-be-scanned part of the patient.

Figure 4:
FIG. 4 is a schematic perspective view of a 3D perspective indicator obtained after extending and modifying the embodiment shown in FIG. 2.
Figure 4:
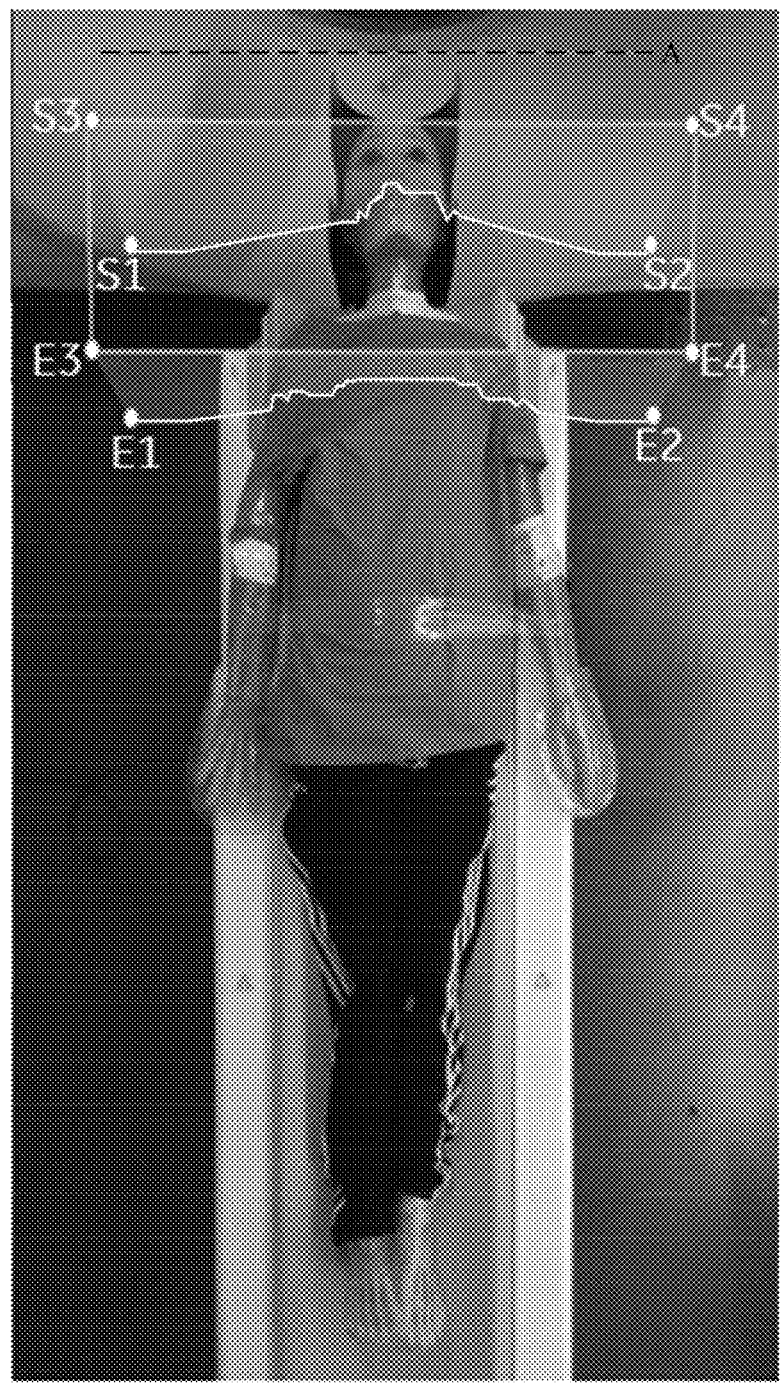

Specifically, as shown in FIG. 4, the upper boundary reference points may be set as two reference points S1 and S2 across the patient structure model, and the lower boundary reference points may also be additionally or alternatively set as two reference points E1 and E2 across the patient structure model. A distance between S1 and S2 and a distance between E1 and E2 may be greater than a maximum width of the patient structure model.

Furthermore, as shown in FIG. 4, the two upper boundary reference points S1, S2 and/or two lower boundary reference points E1, E2 may be forward-projected onto the auxiliary plane to obtain two upper boundary auxiliary points S3, S4 and/or two lower boundary auxiliary points E3, E4.

It should be particularly noted that although the upper boundary reference points, lower boundary reference points, upper boundary auxiliary points, and lower boundary auxiliary points in FIG. 4 are each of two points and distributed across the patient structure model, other numbers and distributions of the upper boundary reference points, lower boundary reference points, upper boundary auxiliary points, and lower boundary auxiliary points are not excluded in actual operation.

FIG. 4 shows an example of neck scanning with the head as the start position, where the start position of scanning is defined to be in the upper boundary plane where S1, S2, S3, and S4 are located, and the end position of scanning is defined to be in the lower boundary plane where E1, E2, E3, and E4 are located. Meanwhile, boundaries formed by S1, S3, E3, and E1 and boundaries formed by S2, S4, E4, and E2 further define the scanning range in an X-axis direction in the CT coordinate system.

Thus, in the method 100 for generating a 3D perspective indicator according to the present invention, the 3D perspective indicator is further constructed as a virtual perspective "box," where the scanning range of CT scanning on the patient is in this perspective "box," so as to present and control the scanning range more accurately, Moreover, it can be clearly seen from FIG. 4 that the contour of the patient's body is added to the bottom of the virtual perspective "box"

to serve as part of a bottom contour line. Such a 3D perspective indicator better helps the operator to generate a 3D perspective impression of the patient's body on a 2D image.

It should be noted that FIG. 2 and FIG. 4 show a physical human model, rather than the patient structure model described herein or the real patient. The physical human model is merely intended to schematically show the approximate position of the patient structure mode and the real patient.

In addition, FIG. 2 and FIG. 4 both show an example of neck scanning with the head as the start position, but those skilled in the art should know that scanning of other parts is similar.

In the method 100 for generating a 3D perspective indicator according to the present invention, referring to FIG. 2, the upper boundary plane and the lower boundary plane may be separately moved or simultaneously moved in the scanning direction.

For the method 100 for generating a 3D perspective indicator in the present invention, when the upper boundary plane and/or lower boundary plane moves in the scanning direction, the upper contour line L1 and/or lower contour line L2 changes in real time with the to-be-scanned part of the patient. Moreover, such real-time change is continuous.

According to an embodiment of the present invention, a 3D perspective indicator for a CT system is accordingly provided, which includes an upper contour line L1 and a lower contour line L2, an upper boundary plane and a lower boundary plane, and an auxiliary plane shown in FIG. 2.

The 3D perspective indicator according to the present invention may further include a patient structure model, where the patient structure model is extracted from a point cloud. The point cloud has been described above, and will not be elaborated herein. The upper contour line L1 and the lower contour line L2 are respectively intersecting lines of the patient structure model with the upper boundary plane and the lower boundary plane, as shown in FIG. 2.

The 3D perspective indicator according to the present invention may further include a main reference plane, as shown in FIG. 3. The main reference plane is generated in a coordinate system space of the CT system and is parallel to the auxiliary plane. The patient structure model is on the main reference plane and, together with the main reference plane, defines a shape of the to-be-scanned part.

Optionally, the main reference plane may be located on a highest surface of a scanning bed. Refer to FIG. 3 for details.

Further, in the 3D perspective indicator according to the present invention, the upper contour line L1 and/or lower contour line L2 may intersect the main reference plane at upper boundary reference points and/or lower boundary reference points. The upper contour line L1 and/or the lower contour line L2 matches a contour of the to-be-scanned part of the patient.

As shown in FIG. 4, the upper boundary reference points may be two reference points S1 and S2 across the patient structure model, and a distance therebetween is greater than a maximum width of the patient structure model. Additionally or alternatively, the lower boundary reference points may also be two reference points E1 and E2 across the patient structure model, and a distance therebetween is also greater than the maximum width of the patient structure model.

Further, the 3D perspective indicator shown in FIG. 4 further includes two upper boundary auxiliary points S3, S4 and/or two lower boundary auxiliary points E3, E4, which are respectively points obtained by forward-projecting the two upper boundary reference points S1, S2 and/or two lower boundary reference points E1, E2 onto the auxiliary plane.

Referring to FIG. 2, in the 3D perspective indicator in the present invention, the upper boundary plane and the lower boundary plane thereof may separately move or simultaneously move in the scanning direction.

When the upper boundary plane and/or the lower boundary plane moves in the scanning direction, the upper contour line L1 and/or the lower contour line L2 will change in real time with the to-be-scanned part of the patient. Moreover, such real-time change is continuous.

The aforementioned 3D perspective indicator according to the present invention and various alternative embodiments and examples thereof correspond to the method 100 for generating a 3D perspective indicator according to the present invention, many design details of the method 100 apply equally to the 3D perspective indicator and various alternative embodiments thereof, and the 3D perspective indicator and various alternative embodiments thereof can achieve all technical effects achievable by the method 100.

According to an embodiment of the present invention, a method for controlling a scanning range in a CT system is further provided.

Figure 5:
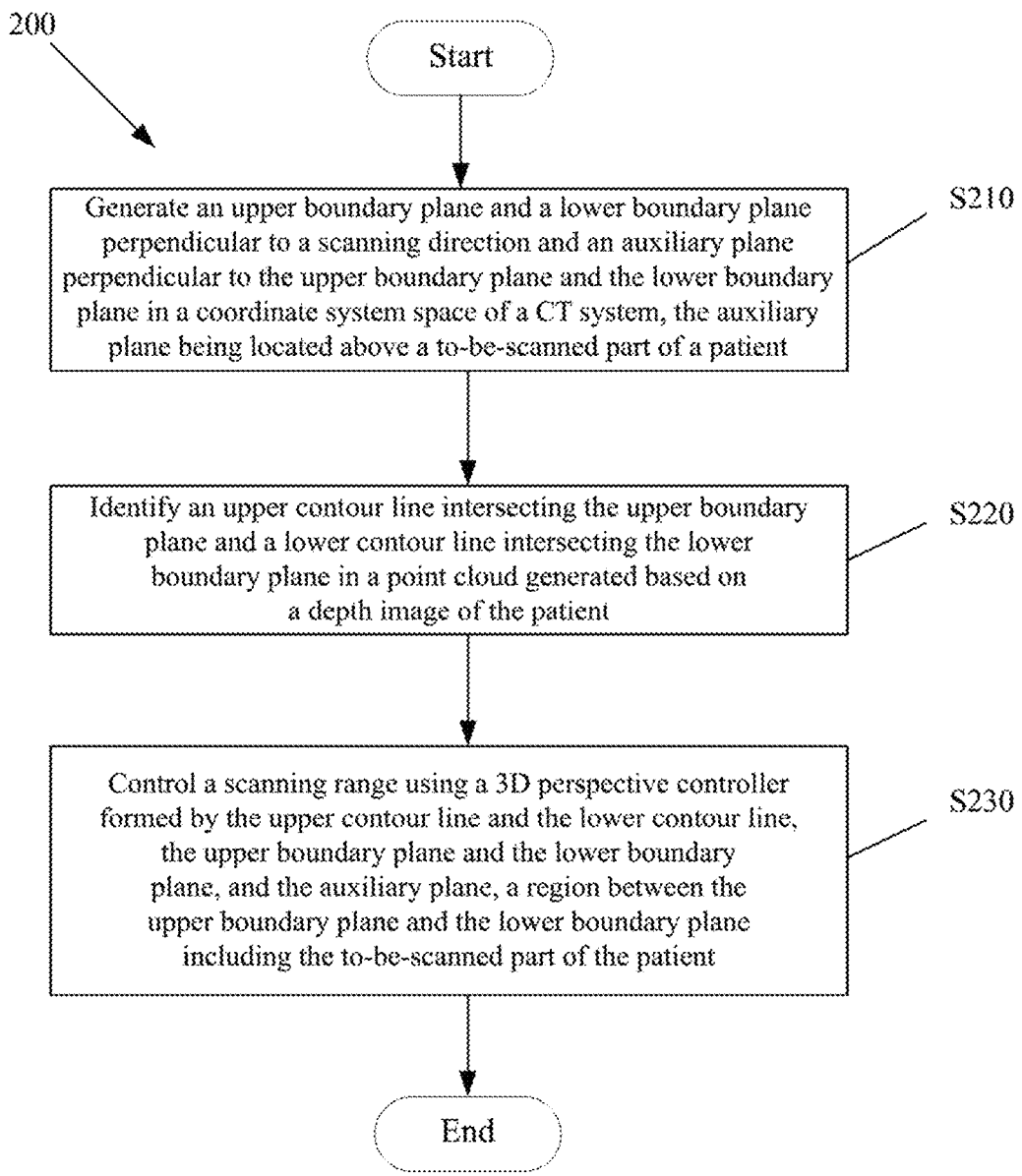
FIG. 5 is a flowchart of a method for controlling a scanning range in a CT system according to an exemplary embodiment of the present invention.

FIG. 5 shows a method 200 for controlling a scanning range in a CT system according to an exemplary embodiment of the present invention. The method 200 may include steps S210 to S230.

As shown in FIG. 5, step S210: generate an upper boundary plane and a lower boundary plane perpendicular to a scanning direction and an auxiliary plane perpendicular to the upper boundary plane and the lower boundary plane in a coordinate system space of the CT system, the auxiliary plane being located above a to-be-scanned part of a patient; reference may be made to FIG. 2 as well.

Next, step S220: generate an upper boundary plane and a lower boundary plane perpendicular to a scanning direction and an auxiliary plane perpendicular to the upper boundary plane and the lower boundary plane in a coordinate system space of the CT system, the auxiliary plane being located above a to-be-scanned part of a patient.

After the two steps, a 3D perspective indicator represented by an upper contour line L1 and a lower contour line L2, the upper boundary plane and the lower boundary plane, and the auxiliary plane is actually generated. Finally, step S230: control a scanning range using the 3D perspective indicator, a region between the upper boundary plane and the lower boundary plane including the to-be-scanned part of the patient.

The method for controlling a scanning range in a CT system described above is actually a practical application of the 3D perspective indicator generated according to the present invention. An operator can conveniently view and modify a scanning range in a CT system through such a 3D perspective indicator superimposed on a 2D video (or image).

Such a 3D perspective indicator does not produce misguidance on the operator caused by perspective distortion, so that the operator can complete all pre-scanning work in a scanning room. Control operations on the scanning range are made more intuitive, accurate, and convenient, thereby greatly improving operation efficiency.

As described above, the method 200 is a practical application of the 3D perspective indicator generated according to the present invention. A 3D perspective indicator can thus be generated using all alternative embodiments and examples of the method 100 for generating a 3D perspective indicator described above, and then the scanning range can be controlled in real time using the generated 3D perspective indicator. Accordingly, when the design details of the method 100 for generating a 3D perspective indicator described above are applied to the method 200 for controlling a scanning range described above, similar or identical functions and effects can be achieved.

In addition, for the method 200 for controlling a scanning range described above, referring to FIG. 2, the scanning range may be displayed through a display unit, and the scanning range may be controlled by translating the upper boundary plane and/or the lower boundary plane up and down in the scanning direction on the display unit.

The display unit may include various displays, such as a touch screen display, so that the operator only needs to drag or click on a touch screen to conveniently implement various control operations on the scanning range.

Further, for the method 200 for controlling a scanning range described above, referring to FIG. 4, the scanning range is displayed through a display unit, and the scanning range is controlled by setting on the display unit at least one of the two upper boundary auxiliary points S3, S4 and/or at least one of the two lower boundary auxiliary points E3, E4 and/or any point in a connection line S3-S4 of the two upper boundary auxiliary points and/or any point in a connection line E3-E4 of the two lower boundary auxiliary points.

Further, for the method 200 for controlling a scanning range described above, referring to FIG. 4, the scanning range is displayed through a display unit, and the entire scanning range is controlled to translate up and down in the scanning direction by controlling on the display unit a connection line between the upper boundary auxiliary point S3/S4 and a corresponding lower boundary auxiliary point E3/E4 on the same side or any point in the connection line. Specifically, for example, the entire 3D perspective box (3D perspective indicator) may be selected by clicking a connection line S3-E3 between auxiliary points S3, E3 on the same side or any point in the connection line S3-E3, and the 3D perspective box may be dragged in the scanning direction, so as to control the scanning range.

According to an embodiment of the present invention, a computer-readable storage medium is further provided, having encoded instructions recorded thereon, where when the instructions are executed, the method for generating a 3D perspective indicator and the method for controlling a scanning range in a CT system based on the generated 3D perspective indicator described above are performed. The computer-readable storage medium may include a hard disk drive, a floppy disk drive, a CD-read/write (CD-R/W) drive, a digital versatile disc (DVD) drive, a flash drive, and/or a solid-state storage device. The computer-readable storage medium may be installed in a CT system, or may be installed in a separate control device or computer that remotely controls the CT system.

According to an embodiment of the present invention, an apparatus capable of implementing the method for controlling a scanning range described above is further provided.

Figure 6:
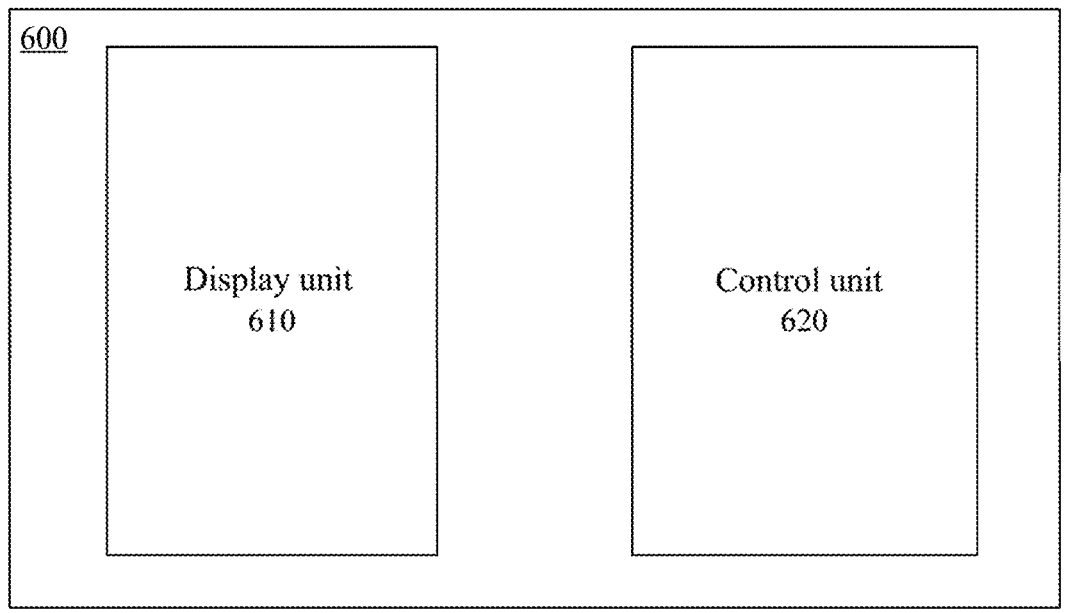
FIG. 6 is a schematic block diagram of an apparatus for controlling a scanning range in a CT system according to an exemplary embodiment of the present invention.

FIG. 6 shows an apparatus 600 for controlling a scanning range in a CT system according to an exemplary embodiment of the present invention. The apparatus 600 includes a display unit 610 and a control unit 620.

The display unit 610 is configured to display a scanning range represented by an upper contour line L1 and a lower contour line L2, an upper boundary plane and a lower boundary plane, and an auxiliary plane, as shown in FIG. 2. The display unit 610 may include any display device, such as a touch screen display.

Referring to FIG. 2 as well, the control unit 620 may be configured to implement the following: generating an upper boundary plane and a lower boundary plane perpendicular to a scanning direction and an auxiliary plane perpendicular to the upper boundary plane and the lower boundary plane in a coordinate system space of the CT system, the auxiliary plane being located above a to-be-scanned part of a patient; and identifying an upper contour line L1 intersecting the upper boundary plane and a lower contour line L2 intersecting the lower boundary plane in a point cloud generated based on a depth image of the patient. A region between the upper boundary plane and the lower boundary plane includes the to-be-scanned part of the patient.

Figure 7:
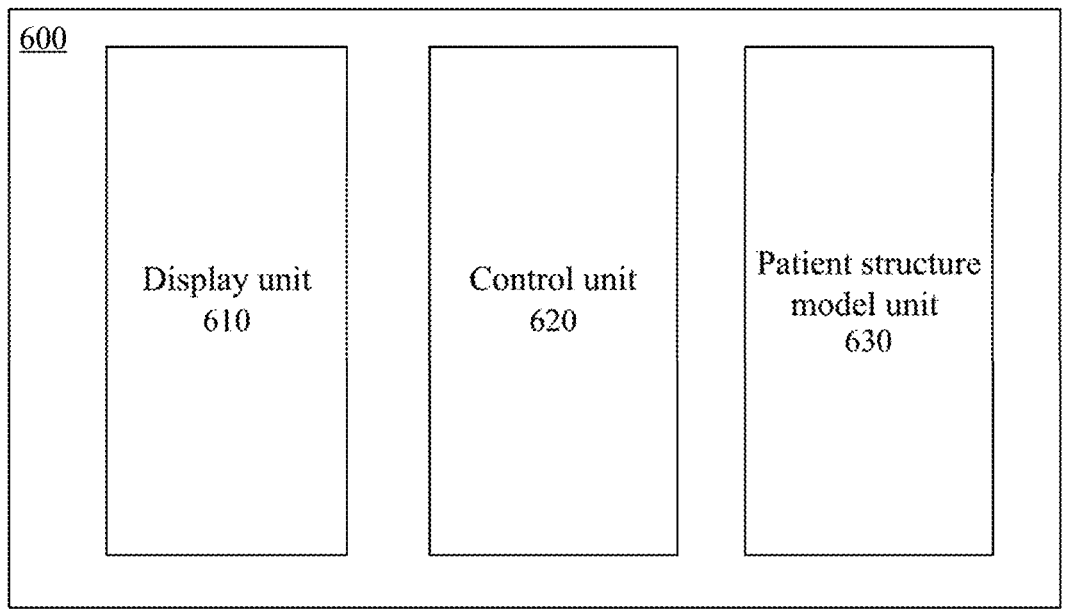
FIG. 7 is a schematic block diagram of an apparatus for controlling a scanning range in a CT system obtained after extending and modifying the embodiment shown in FIG. 6.

Further, as shown in FIG. 7, the apparatus 600 for controlling a scanning range in a CT system according to the present invention may further include a patient structure model unit 630, configured to extract a patient structure model from the point cloud. The upper contour line L1 and the lower contour line L2 are respectively intersecting lines of the patient structure model with the upper boundary plane and the lower boundary plane, as shown in FIG. 2.

Further, the control unit 620 may further be configured to generate a main reference plane parallel to the auxiliary plane in the coordinate system space of the CT system, as shown in FIG. 3. The patient structure model is on the main reference plane and, together with the main reference plane, defines a shape of the to-be-scanned part.

Although the main reference plane shown in FIG. 3 is generated on a highest surface of a scanning bed, the main reference plane may also be generated at other positions as long as the patient structure model is on the main reference plane.

Further, the upper contour line L1 and/or lower contour line L2 may intersect the main reference plane at upper boundary reference points and/or lower boundary reference points, and the upper contour line L1 and/or the lower contour line L2 matches a contour of the to-be-scanned part of the patient.

Specifically, as shown in FIG. 4, the upper boundary reference points and/or the lower boundary reference points may be two reference points (S1/S2 and E1/E2) across the patient structure model, and a distance therebetween may be greater than a maximum width of the patient structure model.

Moreover, points obtained by forward-projecting the two upper boundary reference points S1, S2 and/or two lower boundary reference points E1, E2 onto the auxiliary plane are two upper boundary auxiliary points S3, S4 and/or two lower boundary auxiliary points E3, E4.

The control unit 620 may control the scanning range by translating the upper boundary plane and/or the lower boundary plane up and down in the scanning direction on the display unit 610.

Particularly, when the control unit 620 controls the upper boundary plane and/or the lower boundary plane to move in the scanning direction, the upper contour line L1 and/or the lower contour line L2 changes in real time with the to-be-scanned part of the patient. Such real-time change is continuous.

The control unit 620 may control the scanning range by setting on the display unit 610 at least one of the two upper boundary auxiliary points S3, S4 and/or at least one of the two lower boundary auxiliary points E3, E4 and/or any point in a connection line S3-S4 of the two upper boundary auxiliary points and/or any point in a connection line E3-E4 of the two lower boundary auxiliary points.

The control unit 620 may control the entire scanning range to translate up and down in the scanning direction by controlling on the display unit 610 a connection line (for example, S3-E3 or S4-E4) between the upper boundary auxiliary point and a corresponding lower boundary auxiliary point on the same side or any point in the connection line.

The aforementioned control unit 620 actually further implements a calculation function of the scanning range, and the calculation function may also be implemented by another separate module. Specifically, 51, S2, S3, S4 and E1, E2, E3, E4 are set so that first, a scanning range value is defined in a CT coordinate system, then the control unit 620 further converts the scanning range value into a pixel on a 2D video (or image), and the exact position of the 3D perspective indicator superimposed on the 2D video (or image) can be generated through the pixel. When an operator modifies the scanning range on the display unit 620, the control unit 620 or another module configured to implement the calculation function converts the aforementioned pixel position into a scanning range value in the CT coordinate system and sends the scanning range value to the CT system for subsequent processing or required operations.

The aforementioned apparatus 600 and various alternative embodiments thereof correspond to the method for controlling a scanning range in a CT system according to the present invention, many design details in the method for controlling a scanning range apply equally to the apparatus 600 and various alternative embodiments thereof, and identical or similar functions and effects can be achieved, which will not be described herein again.

The apparatus and method for controlling a scanning range in a CT system according to the present invention both can be applied to a CT system to enable an operator to intuitively and precisely control a CT scanning range in real time, and meanwhile can improve working efficiency and provide better nursing experience to a patient.

According to an embodiment of the present invention, a CT system is further provided, which includes the apparatus for controlling a scanning range described above. However, it should be noted that the apparatus for controlling a scanning range in a CT system according to the present invention is not necessarily installed in the CT system, but may also be independent of the CT system. In both cases, the scanning range can be controlled intuitively and precisely in real time.

Up to this point, a 3D perspective indicator for a CT system and a generation method therefor as well as a method and an apparatus for controlling a scanning range in a CT system according to the present invention have been described, and a CT system using the apparatus and a computer-readable storage medium capable of implementing the method have also been introduced.

By means of the present invention, when CT scanning is performed in a CT system, an operator views and modifies a scanning range on a real-time image or video, so that misguidance caused by perspective distortion can be eliminated, the operator can judge more intuitively and precisely whether the scanning range is suitable for a patient, and if needed, the operator can immediately modify the scanning range to an appropriate range. Compared with the conventional method that requires a laser lamp to set scanning baselines and checks a scanning range through parameters on a console outside a scanning room, the present invention provides greatly improved operator efficiency. The present invention reduces workload, better achieves standardization, and eliminates manual errors that are present in the conventional method. Moreover, since the scanning range is checked on a real-time video or image in the scanning room, the operator can complete all pre-scanning work in the scanning room and can spend more time on the patient, which also helps to improve patient experience during CT scanning.

Some exemplary embodiments have been described above. However, it should be understood that various modifications can be made to the exemplary embodiments described above without departing from the spirit and scope of the present invention. For example, an appropriate result can be achieved if the described techniques are performed in a different order and/or if the components of the described system, architecture, device, or circuit are combined in other manners and/or replaced or supplemented with additional components or equivalents thereof; accordingly, the modified other embodiments also fall within the protection scope of the claims.

The invention claimed is:

1. A method for generating a 3D perspective indicator in a CT imaging system, the method comprising:
   generating an upper boundary plane and a lower boundary plane perpendicular to a scanning direction and an auxiliary plane perpendicular to the upper boundary plane and the lower boundary plane in a coordinate system space of the CT imaging system, the auxiliary plane being located above a to-be-scanned region of a patient; and
   identifying an upper contour line intersecting the upper boundary plane and a lower contour line intersecting the lower boundary plane in a point cloud generated based on a depth image of the patient;
   wherein the 3D perspective indicator comprises the upper contour line and the lower contour line, the upper boundary plane and the lower boundary plane, and the auxiliary plane.

2. The method according to claim 1, further comprising extracting a patient structure model from the point cloud, the upper contour line and the lower contour line being respectively intersecting lines of the patient structure model with the upper boundary plane and the lower boundary plane.

3. The method according to claim 2, further comprising generating a main reference plane parallel to the auxiliary plane in the coordinate system space of the CT imaging system, the patient structure model being on the main reference plane and, together with the main reference plane, defining a shape of the to-be-scanned region.

4. The method according to claim 3, wherein the main reference plane is generated on a top surface of a scanning table.

5. The method according to claim 3, wherein the upper contour line and/or lower contour line intersects the main reference plane at upper boundary reference points and/or lower boundary reference points, and the upper contour line and/or the lower contour line matches a contour of the to-be-scanned region of the patient.

6. The method according to claim 5, wherein the upper boundary reference points and/or the lower boundary reference points are two reference points across the patient structure model, and a distance therebetween is greater than a maximum width of the patient structure model.

7. The method according to claim 6, further comprising forward-projecting the two upper boundary reference points and/or two lower boundary reference points onto the auxiliary plane to obtain two upper boundary auxiliary points and/or two lower boundary auxiliary points.

8. The method according to claim 1, wherein the upper boundary plane and the lower boundary plane are capable of separately moving or simultaneously moving in the scanning direction.

9. The method according to claim 8, wherein when the upper boundary plane and/or the lower boundary plane moves in the scanning direction, the upper contour line and/or the lower contour line changes in real time with the to-be-scanned part region of the patient.

10. The method according to claim 9, wherein the real-time change is continuous.

11. A 3D perspective indicator for a CT imaging system, comprising:
- an upper boundary plane and a lower boundary plane, which are in a coordinate system space of the CT imaging system and perpendicular to a scanning direction;
- an auxiliary plane being in the coordinate system space of the CT imaging system and perpendicular to the upper boundary plane and the lower boundary plane, the auxiliary plane being located above a to-be-scanned region of a patient; and
- an upper contour line and a lower contour line, which are located in a point cloud generated based on a depth image of the patient and respectively intersect the upper boundary plane and the lower boundary plane.

12. A method for controlling a scanning range in a CT imaging system, the method comprising:
- generating a 3D perspective indicator in the CT imaging system; and
- controlling a scanning range using the 3D perspective indicator, the 3D perspective indicator including an upper contour line and a lower contour line, an upper boundary plane and a lower boundary plane, and an auxiliary plane representing the scanning range, wherein a region between the upper boundary plane and the lower boundary plane comprises the to-be-scanned region of the patient.

13. The method according to claim 12, wherein the scanning range is displayed through a display unit, and the scanning range is controlled by translating the upper boundary plane and/or the lower boundary plane up and down in the scanning direction on the display unit.

14. The method according to claim 12, wherein the scanning range is displayed through a display unit, and the scanning range is controlled by setting on the display unit at least one of the two upper boundary auxiliary points and/or at least one of the two lower boundary auxiliary points and/or any point in a connection line of the two upper boundary auxiliary points and/or any point in a connection line of the two lower boundary auxiliary points.

15. The method according to claim 12, wherein the scanning range is displayed through a display unit, and the entire scanning range is controlled to translate up and down in the scanning direction by controlling on the display unit a connection line between the upper boundary auxiliary point and a corresponding lower boundary auxiliary point on the same side or any point in the connection line.

16. An apparatus for controlling a scanning range in a CT imaging system, the apparatus comprising:
- a display unit, configured to display a scanning range represented by an upper contour line and a lower contour line, an upper boundary plane and a lower boundary plane, and an auxiliary plane; and
- a control unit, configured to:
  - generate an upper boundary plane and a lower boundary plane perpendicular to a scanning direction and an auxiliary plane perpendicular to the upper boundary plane and the lower boundary plane in a coordinate system space of the CT imaging system, the auxiliary plane being located above a to-be-scanned region of a patient; and
  - identify an upper contour line intersecting the upper boundary plane and a lower contour line intersecting the lower boundary plane in a point cloud generated based on a depth image of the patient;
  - wherein a region between the upper boundary plane and the lower boundary plane comprises the to-be-scanned region of the patient.

17. The apparatus according to claim 16, wherein the control unit is further configured to control the scanning range by translating the upper boundary plane and/or the lower boundary plane up and down in the scanning direction on the display unit.

18. The apparatus according to claim 17, wherein when the control unit controls the upper boundary plane and/or the lower boundary plane to move in the scanning direction, the upper contour line and/or the lower contour line changes in real time with the to-be-scanned region of the patient.

19. The apparatus according to claim 18, wherein the real-time change is continuous.

* * * * *